(12) United States Patent
Chopra et al.

(10) Patent No.: US 10,381,134 B2
(45) Date of Patent: Aug. 13, 2019

(54) STRAIN GAUGE POLYMER COMPRISING PHOTOCHROMIC COLORANT

(71) Applicant: XEROX CORPORATION, Norwalk, CT (US)

(72) Inventors: Naveen Chopra, Oakville (CA); Rachel Prestayko, Hamilton (CA); Sarah J. Vella, Milton (CA)

(73) Assignee: XEROX CORPORATION, Norwalk, CT (US)

( * ) Notice: Subject to any disclaimer, the term of this patent is extended or adjusted under 35 U.S.C. 154(b) by 213 days.

(21) Appl. No.: 14/982,752

(22) Filed: Dec. 29, 2015

(65) Prior Publication Data

US 2017/0186514 A1 Jun. 29, 2017

(51) Int. Cl.
| | |
|---|---|
| *C08L 9/02* | (2006.01) |
| *C08L 9/06* | (2006.01) |
| *C08J 3/12* | (2006.01) |
| *C08J 3/20* | (2006.01) |
| *H01B 3/44* | (2006.01) |
| *H01B 7/36* | (2006.01) |
| *C07D 413/02* | (2006.01) |
| *C07D 491/04* | (2006.01) |
| *C08K 5/3417* | (2006.01) |
| *C07D 491/107* | (2006.01) |

(52) U.S. Cl.
CPC .......... *H01B 7/361* (2013.01); *C07D 413/02* (2013.01); *C07D 491/04* (2013.01); *C07D 491/107* (2013.01); *C08J 3/12* (2013.01); *C08J 3/203* (2013.01); *C08K 5/3417* (2013.01); *C08L 9/02* (2013.01); *C08L 9/06* (2013.01); *H01B 3/441* (2013.01); *C08J 2355/02* (2013.01); *Y10T 428/31855* (2015.04)

(58) Field of Classification Search
CPC .. C08J 3/12; C08J 3/203; H01B 3/441; H01B 7/361; C08K 5/3417; C08L 55/02; C08L 9/02; C08L 9/06; C07D 498/10; C07D 498/20; C07D 491/107; C07D 491/04; C07D 413/02; Y10T 428/31855
See application file for complete search history.

(56) References Cited

U.S. PATENT DOCUMENTS

| | | | | |
|---|---|---|---|---|
| 3,168,593 | A * | 2/1965 | Fremon | C08F 279/04 525/316 |
| 3,322,542 | A * | 5/1967 | Ullman | G03C 1/73 359/241 |
| 3,442,980 | A * | 5/1969 | Grabowski | C08K 5/09 524/112 |
| 3,501,410 | A * | 3/1970 | Tamblyn | G03C 1/685 252/586 |
| 3,856,728 | A * | 12/1974 | Abramoff | C08K 5/00 252/400.24 |
| 4,831,142 | A * | 5/1989 | Kwak | C07D 498/10 544/71 |
| 4,913,544 | A * | 4/1990 | Rickwood | C07D 498/10 252/586 |
| 5,411,679 | A | 5/1995 | Kumar | |
| 5,501,945 | A | 3/1996 | Kanakkanatt | |
| 2004/0259975 | A1 | 12/2004 | Robillard | |
| 2005/0012081 | A1* | 1/2005 | Yasuda | C08K 5/357 252/586 |
| 2006/0033088 | A1* | 2/2006 | Kim et al. | B32B 17/10018 252/586 |
| 2010/0215599 | A1 | 8/2010 | Giron et al. | |

FOREIGN PATENT DOCUMENTS

| | | | |
|---|---|---|---|
| CN | 102585423 A * | 7/2012 | |
| EP | 0493814 A2 * | 7/1992 | .............. C08L 55/02 |

OTHER PUBLICATIONS

Machine translation of CN102585423. Retrieved Apr. 11, 2018.*
Krongauz et al. "Use of Photochromic Spiropyran as a Molecular Probe of Large Strain in Polycarbonate". High Energy Chemistry, vol. 43, No. 5, (2009); pp. 400-405.*
"Calibre Polycarbonate Resins Product Information Guide". Dow Plastics, (2001); pp. 1-48.*
Kulich et al. "Acrylonitrile-Butadiene-Styrene (ABS) Polymers". Kirk-Othmer Encyclopedia of Chemical Technology, (2003); pp. 414-438.*
"Materials Data Book". Cambridge University Engineering Department, (2003); pp. 1-37.*
"Material: ABS-acrylonitrile butadiene styrene". http://designinsite.dk/htmsider/m0007.htm, (2003).*
V.A. Krongauz, et al.: "Use of Photochromic Spiropyran as a Molecular Probe of Large Strain in Polycarbonate" High Energy Chemistry, vol. 43, No. 5, Mar. 16, 2009, pp. 400-405 (6 pages).
Hal S. Blair, et al.: "Photomechanical effects in polymers containing 6'-nitro-1,3,3-trimethyl-spiro-(2'H-1'-benzopyran-2,2'-indoline)" Polymer, 1982, vol. 23, Mar. 23, 1981, pp. 779-783 (5 pages).
Brent R. Crenshaw, et. al.: "Self-Assessing Photoluminescent Polyurethanes" Department of Macromolecular Science and Engineering and Department of Chemistry, Case Wester Reserve University; Sep. 26, 2006, pp. 9581-9589 (9 pages).
CES 2012 EDUPACK: "ABS (heat resistant, injection molding)", pp. 1-3.
Meng, Xiao et al: "Visible Mechanochromic Responses of Spiropyrans in Crystals via Pressure-Induced Isomerization"; Royal Society of Chemistry Chemical Communication; Apr. 27, 2015, vol. 51, pp. 9320-9323 (4 pages).

* cited by examiner

*Primary Examiner* — Prashant J Khatri

(74) *Attorney, Agent, or Firm* — Pillsbury Winthrop Shaw Pittman LLP

(57) ABSTRACT

A composite manufacture includes an extrudable thermoplastic matrix and a photochromic colorant, the photochromic colorant conferring to the composite a reversible strain-induced color change property. Methods include adding photochromic colorant to an extrudable thermoplastic polymer matrix to form a mixture, heating the mixture to form a composite, the photochromic colorant conferring to the composite a reversible strain-induced color change property. The composite manufactures can be used in cable coatings permitting visual detection of mechanical stresses in a wire based on the reversible strain-induced color change property.

20 Claims, No Drawings

STRAIN GAUGE POLYMER COMPRISING PHOTOCHROMIC COLORANT

BACKGROUND

The present disclosure relates to detecting strain in polymers. More particularly, the present disclosure relates to composite structures in which strain is detectable upon visual inspection.

Measurement of strain in materials is typically done with instrumentation. Very few examples exist of materials that can give a visual measure of strain. One example is a liquid crystal system, which is very dependent on thickness, and is a costly option. There is a need for low cost visual indicators of strain in polymeric materials.

SUMMARY

In some aspects, embodiments herein relate to composite manufactures comprising an extrudable thermoplastic matrix and a photochromic colorant, wherein the photochromic colorant confers to the composite a reversible strain-induced color change property.

In some aspects, embodiments herein relate to methods comprising adding photochromic colorant to an extrudible thermoplastic polymer matrix to form a mixture, heating the mixture to form a composite, wherein the photochromic colorant confers to the composite a reversible strain-induced color change property.

In some aspects, embodiments herein relate to cable coatings permitting visual detection of mechanical stresses in a wire, the cable coating comprising a composite comprising an acrylonitrile-butadiene-styrene matrix and a photochromic colorant, wherein the photochromic colorant confers to the composite a reversible strain-induced color change property.

DETAILED DESCRIPTION

In embodiments, there are provided composite manufactures comprising an extrudable thermoplastic matrix and a photochromic colorant, wherein the photochromic colorant is selected to confer to the composite a reversible strain-induced color change property.

As used herein, "extrudable" refers to a thermoplastic matrix material capable of melt extrusion, such as through a melt flow index (MFI) extruder, or similar instrument that forces a thermoplastic polymer melt through an orifice. The orifice need not be circular in shape and may include any geometry such as square, rectangular, triangular, and the like. Any of these geometries can also be obtained in a hollow form, such as a hollow cylinder. Extrudable thermoplastic matrix materials may have a polymer melt temperature in a range from about 50° C. to about 400° C., or about 750° C. to about 340° C.

As used herein, "thermoplastic matrix" refers to a polymer matrix component of a composite material. The thermoplastic matrix may be the bulk material of the composites disclosed herein. In embodiments, composite materials may also combine more than one type of thermoplastic matrix. The thermoplastic matrix may be selected to have certain flexing properties, such as the material can have a flexural modulus of less 2 GPa, such as less than 1 GPa, or less than 0.5 GPa.

In embodiments, the extrudable thermoplastic matrix may be acrylonitrile-butadiene-styrene. In embodiments, the ratio of component acrylonitrile, butadiene and styrene may be about 15 to about 35%:about 5 to about 30%:about 40 to about 60%, respectively In other embodiments, the extrudable thermoplastic matrix may be based on acrylic polymers, such as poly(methyl methacrylate) (PMMA), nylon, polylactic acid (PLA), polybenzimidazole (PBI), polycarbonate (PC), polyethersulfone (PES), polyetherether ketone (PEEK), polyetherimide (PEI, such as Ultem 9085, from Sabic), polyphenylene oxide (PPO), polypropylene (PP), polyethylene (PE), polystyrene (PS), polyvinyl chloride (PVC), polytetrafluoroethylene (PTFE), polyphenylene oxide, polyphenylsulfone (PPSF, aka Radel R, from Solvay), polycaprolactone. Any of the foregoing extrudable thermoplastic matrix materials may be used in combination or as co-polymers of the above.

As used herein, "photochromic colorant" generally refers to pigments and dyes that may change color upon exposure to irradiation by light. In accordance with embodiments herein, it has been discovered that certain photochromic colorants are responsive to color change not only upon irradiation with light, but also when subjected to physical stresses. In embodiments, the photochromic colorant is selected as the first type whereby color change is also reversible with respect to light-induced color change. Examples of photochromic colorants include, without limitation, triarylmethanes, stilbenes, azastilbenes, nitrones, fulgides, spiropyrans, naphthopyrans, spiro-oxazines, quinones, diarylethenes. In embodiments, any combination of photochromic colorants may be used in the composite structures herein.

In embodiments, photochromic colorants (or dyes and other compounds types) may be selected from various classes, including, without limitation, triarylmethanes, stilbenes, azastilbenes, nitrones, fulgides, spiropyrans, naphthopyrans, spiro-oxazines, quinones, and diarylethenes. In embodiments, photochomic colorants may include those disclosed in Dürr et al., 'Photochromism, Molecules & Systems', Elsevier Publishing 2003.

In embodiments, the photochromic colorant may be a spiropyran or a spirooxazine. In embodiments, the photochromic colorant may have the structure of Formula A:

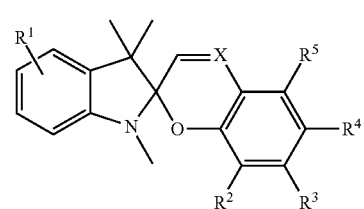

wherein: X is CH or N; $R^1$ may be a halogen or $C_1$-$C_4$ alkoxy; $R^2$, $R^3$, $R^4$, and $R^5$ are independently selected from the group consisting of nitro, halogen, and $C_1$-$C_4$ alkoxy; or any pair of adjacent (i.e., ortho disposed) $R^2$, $R^3$, $R^4$, and $R^5$ taken together can form a further fused phenyl ring. Halogens may include, for example, Cl, Br, I, and F. $C_1$-$C_4$ alkoxy may include methoxy, ethoxy, n-propoxy, isopropoxy, n-butoxy, sec-butoxy, iso-butoxy, and tert-butoxy.

For example, the photochromic colorant may be the structure of Formula 1:

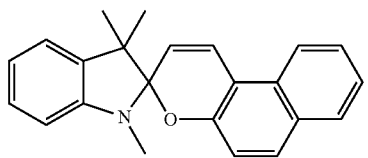

Other compounds of Formula A are shown below in the Examples.

In embodiments, the photochromic colorant may be a triarylmethane, such as: the family of substituted leucocyanides.

In embodiments, the photochromic colorant may be a stilbene, such as: substituted DHP (4a, 4b-dihydrophenanthrenes).

In embodiments, the photochromic colorant may be an azastilbene.

In embodiments, the photochromic colorant may be a nitrone, such as: diarylnitrones.

In embodiments, the photochromic colorant may be a fulgide, such as: diphenylfulgide.

In embodiments, the photochromic colorant may be a spiropyran, such as: 1,3,3-Trimethylindolino-β-naphthopyrylospiran (1).

In embodiments, the photochromic colorant may be a naphthopyran, such as: 3-(2,4-dimethoxyphenyl), 3-(4-methoxyphenyl)-(3H)-benzo(b)furo[2,3-f]-1-benzopyran as disclosed in U.S. Pat. No. 5,411,679, which is incorporated herein by reference in its entirety.

In embodiments, the photochromic colorant may be a spirooxazine, such as: 1,3-dihydro-1,3,3-trimethylspiro[2H-indole-2,3'-[3H]naphtha[2,1-b][1,4]oxazine].

In embodiments, the photochromic colorant may be a diarylethene, such as: 1,2-bis(2-methyl-5-phenyl-3-thienyl)-3,3,4,4,5,5-hexafluorocyclopentene (Tradename DAE-MP (Yamada Chemical)), disclosed in U.S. 2010/0215599 which is incorporated herein by reference in its entirety.

In embodiments, the photochromic colorant may be an azobenzene.

In embodiments, the photochromic colorant may be a quinone, such as 1-phenoxyanthraquinones.

In embodiments, the photochromic colorant is based on an inorganic silver or zinc salt, including halide salts. Examples include, without limitation, silver chloride, sodium chloride, potassium chloride, zinc(II) chloride, cobalt(II) chloride, copper (II) nitrate, mercury(II) chloride, tin(II) chloride. Organic metal salts such as barium napthenate, zinc napthenate, cobalt napthenate, lead napthenate, and antimony (III) napthenate may also be used. Others include those disclosed in U.S. 2004/0259975, which is incorporated herein by reference in its entirety.

In embodiments, the photochromic colorant may be present in an amount in a range from about 0.1 percent by weight of the composite to about 5.0 percent by weight of the composite, or about 0.2 percent to about 3.0 percent by weight of the composite, or about 0.3 to about 1.0 percent by weight of the composite.

In embodiments, the reversible strain-induced color change property is reversible by applying heat to the composite. As used herein "strain-induced color change" means that the composite structure changes in color at the area where the composite is under a physical stress including, but not limited to, bending, flexing, impact, shear stress, and combinations thereof.

In embodiments composite manufactures may take the form of a filament, coating or film. In embodiments, the composite manufacture is a filament. In embodiments, the composite manufacture is a coating. In embodiments, the composite manufacture is a hollow tube designed to coat a wire or a bundle of wires as a cable. In some such embodiments, the color change which is visual to the observers eye may indicate the location of physical stresses on the cable.

In embodiments, the composite manufactures herein may have an elastic modulus in a range from about 0.01 Gigapascal to about 4.0 Gigapascal.

In embodiments there are provided methods comprising adding a photochromic colorant to an extrudable thermoplastic polymer matrix to form a mixture and heating the mixture to form a composite, wherein the photochromic colorant is selected to confer to the composite a reversible strain-induced color change property.

In embodiments, the methods further comprise grinding the composite into pellets. In embodiments, the methods further comprise extruding the pellets in a melt extruder to provide a filament of the composite. In embodiments, the filament may be wound onto a spool for packaging and shipping for downstream use.

In embodiments, a filament may be selected to have a diameter suitable for use in an additive manufacturing (i.e., 3-D printer) apparatus. In such embodiments, methods may further include 3-D printing a three dimensional object using the filament. The resulting three dimensional object may comprise a part where stress assessment is desired when in use. For example, a printed nut/bolt assembly, where the strain on the nut/bolt can be indicated visually by the colour change when tightened by a wrench.

In embodiments, the methods further comprise forming a coating on a cable and/or wire from the composites disclosed herein. The coating process may start from pellets or filaments, or even a paste. Such pastes may be applied to the cable by molding around the cable or dip coating, for example. In embodiments, the composite manufactures in pellet or other form may be further subjected to molding techniques as an alternative to extrusion. Those skilled in the art of composite manufacture will appreciate that other techniques may be used to manipulate the composite manufactures disclosed herein.

In embodiments, any of the aforementioned photochromic colorants may be employed in the methods herein including the photochromic colorant having the structure of Formula 1:

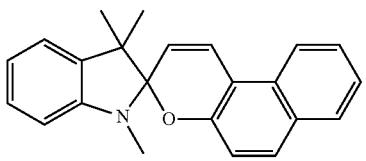

In embodiments, the methods herein may employ the photochromic colorant in an amount in a range from about 0.1 percent by weight of the composite to about 5.0 percent by weight of the composite.

In embodiments, the methods herein that generate composite manufactures may include any further composite manufacturing technique employed in the art. Non-limiting examples of further manipulation of the composite materials include injection molding, blow molding, compression molding, gas injection molding, thermoforming, and extrusion.

In embodiments, there are provided cable coatings permitting visual detection of mechanical stresses in a wire, the cable coating comprising a composite comprising an acrylonitrile-butadiene-styrene matrix and a photochromic colorant, wherein the photochromic colorant confers to the composite a reversible strain-induced color change property. In embodiments, the composite used in cable coating may include a photochromic colorant that is reversible with respect to light-induced color change.

In embodiments, the photochromic colorant used in the cable coating composite has the structure of Formula 1:

1

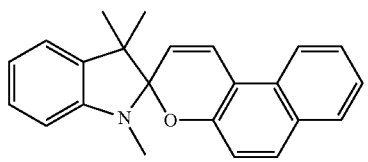

In embodiments, the composite of the cable coating may have the photochromic colorant present in an amount in a range from about 0.1 percent by weight of the composite to about 5.0 percent by weight of the composite. In embodiments, the cable coating may provide reversible strain-induced color change by applying heat to the cable coating.

In embodiments, any object formed from the composite manufactures disclosed herein, including cable coating for wires, may be further coated once in their final form. Such further coatings may be designed to reduce photo-oxidation and other decay upon environmental exposure.

In embodiments, the composite of the cable coating is designed to have a thickness in a range from about 0.1 mm to about 5 mm. As an example, about a 2 mm orifice is suitable for targeting coating of filaments having a diameter of about 1.74 mm.

In exemplary embodiments, there are provided a composite materials comprising acrylonitrile-butadiene-styrene (ABS) blended with a photochromic molecule. The composite may be prepared by melt-mixing, followed by extrusion through a melt flow index machine to furnish a filament. The filament can be flexed and discolored in the area of strain. The discoloration may persist in the film, and can be re-colored when the composite is heated above its softening temperature. Composites of this kind may be useful, for example, in cable coatings for electrical wires.

In particular embodiments, colorant/polymer composites may be prepared by loading about 0.5 wt % spiropyran 1 (1,3,3-Trimethylindolino-β-naphthopyrylospiran) into acrylonitrile-butadiene-styrene (ABS).

1

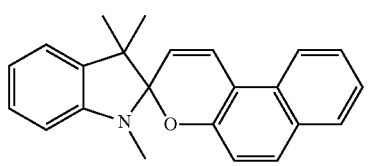

After mixing, the composite may be ground, and fed through a MFI (melt flow index) extruder to furnish about a two to three foot filament, though the length is not so limited.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

This Example describes a process for making an exemplary composite in accordance with embodiments herein comprising about 0.5% of photochromic compound 1 in ABS.

49.75 g of ABS polymer (ABS MG94, Open Source 3D Printing LLC) was fed into a Haake mixer heated to 190° C. 0.25 g photochromic compound 1 (1,3,3-trimethylindolino-beta-napthopyryl, TCI Chemical, product#T0423) was gradually fed into the hopper, and the mixture was compounded at 30 RPM for 30 minutes. After 30 minutes, the Haake mixer was turned off, and the mixture was removed from the mixer. (43.91 g recovered). After cooling, the material was ground up into fine pellets, and fed into a melt flow index (MFI) instrument and equilibrated at 190° C. for six minutes. Next, the pellets were extruded with a 16.96 kg weight through a 2 mm diameter die. The temperature was increased to 200° C. to improve flow. A 4.48 g section of filament with a vibrant magenta color was generated. The filament was 1.07 m long with a diameter ranging from 2.12-2.25 mm.

Example 2

This Example describes a process for making an exemplary composite in accordance with embodiments herein comprising about 0.5% of photochromic compound 1 in PCL (polycaprolactone).

49.75 g of PCL polymer (InstaMorph, Happy Wire Dog, LLC, Scottsdale, Ariz.) was fed into a Haake mixer heated to 62° C. 0.25 g photochromic compound 1 (1,3,3-trimethylindolino-beta-napthopyryl, (T0423) TCI Chemical, Portland, Oreg.) was gradually fed into the hopper, and the mixture was compounded at 30 RPM for 30 minutes. After 30 minutes, the Haake mixer was turned off, and the mixture was removed from the mixer. (43.87 g recovered). After cooling, the material was ground up into fine pellets, and fed into a melt flow index (MFI) instrument and equilibrated at 90° C. for six minutes. Next, the pellets were extruded with a 16.96 kg weight through a 2 mm diameter die. After 9.18 minutes of extrusion, a 5.55 g section of filament with a translucent magenta color was generated. The filament was 1.48 m long with a diameter ranging from 1.67-2.02 mm.

Example 3

This Example describes a process for making an exemplary composite in accordance with embodiments herein comprising about 0.5% of photochromic compound 1 in PLA (polylactic acid).

49.75 g of PLA polymer (Ingeo Biopolymer 4043D, NatureWorks LLC, Minnetonka, Minn.) was fed into a Haake mixer heated to 170° C. 0.25 g photochromic compound 1 (1,3,3-trimethylindolino-beta-napthopyryl, (T0423) TCI Chemical, Portland, Oreg.) was gradually fed into the hopper, and the mixture was compounded at 30 RPM for 30 minutes. After 30 minutes, the Haake mixer was turned off, and the mixture was removed from the mixer. (44.69 recovered). After cooling, the material was ground up into fine pellets, and fed into a melt flow index (MFI) instrument and equilibrated at 170° C. for six minutes. Next, the pellets were extruded with a 16.96 kg weight through a 2 mm diameter die. After 4.83 minutes of extrusion, a 7.24 g section of filament with a opaque magenta color was generated. The filament was 1.91 m long with a diameter ranging from 1.36-2.04 mm.

Examples 4 through 13 below are prophetic, using the ABS polymer matrix as in Example 1, various photochromic dyes available from Sigma Aldrich (spiropyrans and spiroxazines) are expected to perform in substantially the same manner.

Example 4

This Example describes a process for making an exemplary composite in accordance with embodiments herein comprising about 0.5% of photochromic compound 2 (1',3'-Dihydro-1',3',3'-trimethyl-6-nitrospiro [2H-1-benzopyran-2,2'-(2H)-indole] in ABS.

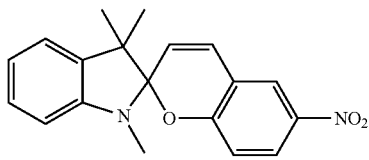

2

49.75 g of ABS polymer (ABS MG94, Open Source 3D Printing LLC, Pleasant Grove, Utah) is fed into a Haake mixer heated to 190° C. 0.25 g photochromic compound 2 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 5

This Example describes a process for making an exemplary composite in accordance with embodiments herein comprising about 0.5% of photochromic compound 3 (1',3'-Dihydro-8-methoxy-1',3',3'-trimethyl-6-nitrospiro [2H-1-benzopyran-2,2'-(2H)-indole] in ABS.

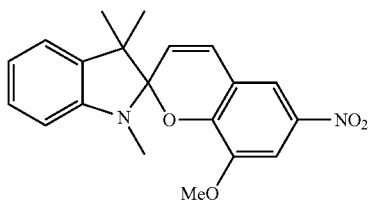

3

49.75 g of ABS polymer (ABS MG94, Open Source 3D Printing LLC, Pleasant Grove, Utah) is fed into a Haake mixer heated to 190° C. 0.25 g photochromic compound 3 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 6

This Example describes a process for making an exemplary composite in accordance with embodiments herein comprising about 0.5% of photochromic compound 4 (1,3-Dihydro-1,3,3-trimethylspiro [2H-indole-2,3'-[3H]napth[2,1-b][1,4]oxazine in ABS.

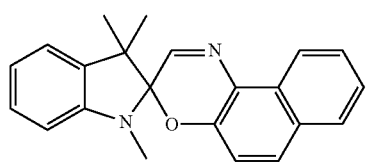

4

49.75 g of ABS polymer (ABS MG94, Open Source 3D Printing LLC, Pleasant Grove, Utah) is fed into a Haake mixer heated to 190° C. 0.25 g photochromic compound 4 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 7

This Example describes a process for making an exemplary composite in accordance with embodiments herein comprising about 0.5% of photochromic compound 5 (6,8-dibromo-1',3'-dihydro-1',3',3'-trimethylspiro[2H-1-benzopyran-2,2'-(2H)-indole] in ABS.

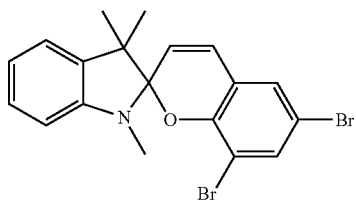

5

49.75 g of ABS polymer (ABS MG94, Open Source 3D Printing LLC, Pleasant Grove, Utah) is fed into a Haake mixer heated to 190° C. 0.25 g photochromic compound 5 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 8

This Example describes a process for making an exemplary composite in accordance with embodiments herein comprising about 0.5% of photochromic compound 6 (5-chloro-1,3-dihydro-1,3,3-trimethylspiro [2H-indole-2,3' [3H]phenanthr [9.10-b][1,4]oxazine in ABS.

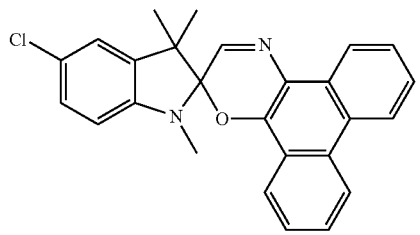

6

49.75 g of ABS polymer (ABS MG94, Open Source 3D Printing LLC, Pleasant Grove, Utah) is fed into a Haake mixer heated to 190° C. 0.25 g photochromic compound 6 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 9

This Example describes a process for making an exemplary composite in accordance with embodiments herein comprising about 0.5% of photochromic compound 7 (6-bromo-1',3'-dihydro-1',3',3'-trimethyl-8-nitrospiro [2H-1-benzopyran-2,2'-(2H)-indole] in ABS.

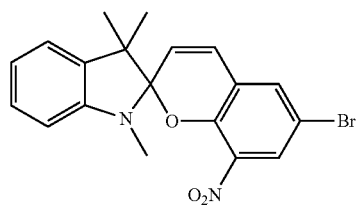

7

49.75 g of ABS polymer (ABS MG94, Open Source 3D Printing LLC, Pleasant Grove, Utah) is fed into a Haake mixer heated to 190° C. 0.25 g photochromic compound 7 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 10

This Example describes a process for making an exemplary composite in accordance with embodiments herein comprising about 0.5% of photochromic compound 8 (5-chloro-1,3-dihydro-1,3,3-trimethylspiro [2H-indole-2,3' [3H]napth [2,1-b][1,4]oxazine in ABS.

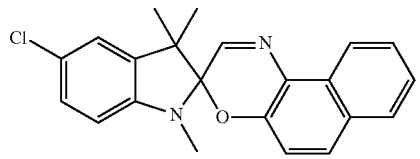

8

49.75 g of ABS polymer (ABS MG94, Open Source 3D Printing LLC, Pleasant Grove, Utah) is fed into a Haake mixer heated to 190° C. 0.25 g photochromic compound 8 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 11

This Example describes a process for making an exemplary composite in accordance with embodiments herein comprising about 0.5% of photochromic compound 9 (1',3'-dihydro-5'-methoxy-1',3',3'-trimethyl-6-nitrospiro[2H-1-benzopyran-2,2'-(2H)-indole] in ABS.

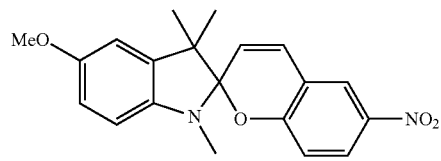

9

49.75 g of ABS polymer (ABS MG94, Open Source 3D Printing LLC, Pleasant Grove, Utah) is fed into a Haake mixer heated to 190° C. 0.25 g photochromic compound 9 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 12

This Example describes a process for making an exemplary composite in accordance with embodiments herein comprising about 0.5% of photochromic compound 10 (1,3-dihydro-1,3,3-trimethylspiro[2H-indole-2,3'-[3H]phenanthr[9,10-b][1,3]oxazine in ABS.

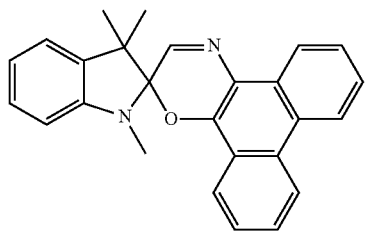

10

49.75 g of ABS polymer (ABS MG94, Open Source 3D Printing LLC, Pleasant Grove, Utah) is fed into a Haake mixer heated to 190° C. 0.25 g photochromic compound 10 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 13

This Example describes a process for making an exemplary composite in accordance with embodiments herein comprising about 0.5% of photochromic compound 11 (5-methoxy-1,3,3-trimethylspiro[indoline-2,3'-[3H]naptho[2,1-b]pyran] in ABS.

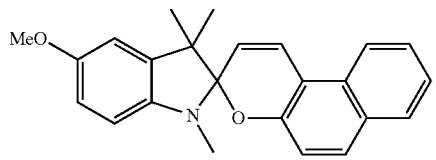

11

49.75 g of ABS polymer (ABS MG94, Open Source 3D Printing LLC, Pleasant Grove, Utah) is fed into a Haake mixer heated to 190° C. 0.25 g photochromic compound 11 is then gradually fed into the hopper, and the mixture is compounded at 30 RPM for 30 minutes. After 30 minutes, the Haake mixer is turned off, and the mixture removed from the mixer. After cooling, the material is ground up into fine pellets, and fed into a melt flow index (MFI) instrument and equilibrated at 190° C. for six minutes. Next, the pellets are extruded with a 16.96 kg weight through a 2 mm diameter die. The temperature is increased to 200° C. to improve flow. A section of filament with a vibrant color is generated.

Example 14

Demonstration of Strain Gauge Properties

A segment of filament from Example 1 was manually flexed by hand to about 60 degrees. The flexed section immediately discolored in the flex zone. After straightening out the material, the discoloration remained. After heating the flexed filament with a heat gun to about 140° C., the flexed filament returned to its original magenta color.

Although embodiments herein provide composites that allow visualization of strain with the eye, the strain can also be measured based on optical density differences between the unbent and bent areas.

Measurement of Optical Density of Photochromic Filament Under Flexural Loads: High-resolution images of the filament were captured using a Keyence digital microscope and printed. L* optical density was measured on the printed images with a GretagMacBeth spectrodensitometer in the crosshaired areas of each image. Due to the curvature and small cross-sectional area of the filament, it was not possible to measure the density on the parts directly. A summary of the L*a*b* values, and density are shown below in Table 1.

TABLE 1

| Degree Bend | L* |
| --- | --- |
| 0° | 59.19 |
| 30° | 80.01 |
| 90° | 70.22 |
| 180° | 72.04 |
| return to 0° | 80.69 |
| heating after return to 0° | 60.37 |

What is claimed is:
1. A composite manufacture comprising:
an extrudable thermoplastic matrix comprises acrylonitrile-butadiene-styrene, wherein the ratio of acrylonitrile:butadiene:styrene is from about 15 to about 35 weight %:about 5 to about 30 weight %:about 40 to about 60 weight %, respectively; and
a photochromic colorant having any one of the following structures:

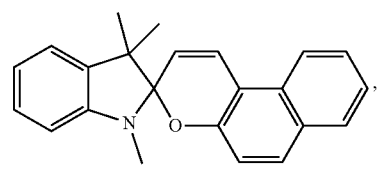

1

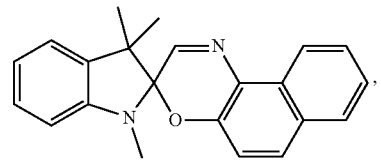

4

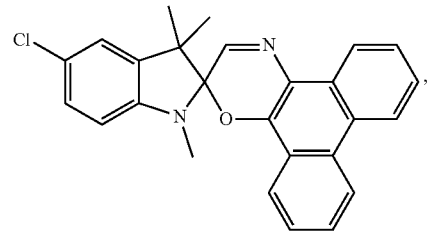

6

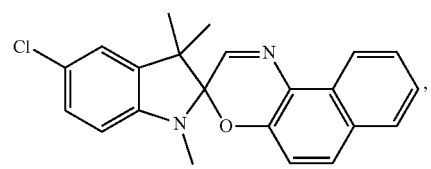

8

-continued

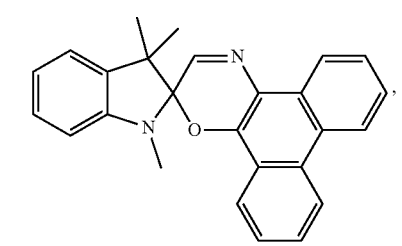
10

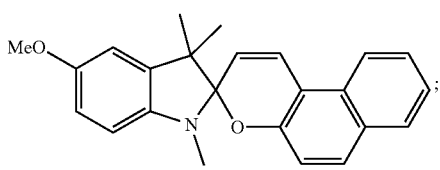
11 wherein the photochromic colorant confers to the composite a reversible strain-induced color change property, further wherein the composite has a flexural modulus in the range of from less than 2 GPa to about 0.1 GPa.

2. The composite manufacture of claim 1, wherein the photochromic colorant having the structure of Formula 1

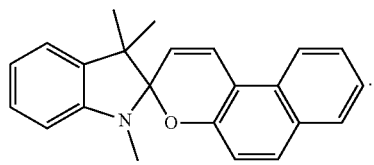
1

3. The composite manufacture of claim 1, wherein the photochromic colorant color change is also reversible with respect to light-induced color change.

4. The composite manufacture of claim 1, wherein the photochromic colorant is present in an amount in a range from about 0.1 percent by weight of the composite to about 5.0 percent by weight of the composite.

5. The composite manufacture of claim 1, wherein reversible strain-induced color change property is reversible by applying heat to the composite.

6. The composite manufacture of claim 1 formed into a filament, film or coating.

7. The composite manufacture of claim 1, wherein the composite has an elastic modulus in a range from about 0.01 Gigapascal to about 4.0 Gigapascal.

8. The composite manufacture of claim 1, wherein the composite has a flexural modulus in the range of less than 1 GPa.

9. The composite manufacture of claim 1, wherein the composite has a flexural modulus in the range of less than 0.5 GPa.

10. A method comprising:
   adding photochromic colorant to an extrudible thermoplastic polymer matrix comprises acrylonitrile-butadiene-styrene to form a mixture, wherein the ratio of acrylonitrile:butadiene:styrene is from about 15 to about 35 weight %:about 5 to about 30 weight %:about 40 to about 60 weight %, respectively;
   heating the mixture to form a composite;
wherein the photochromic colorant having any one of the following structures:

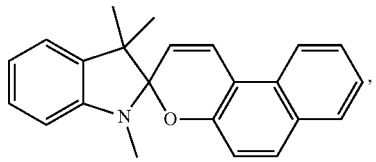
1

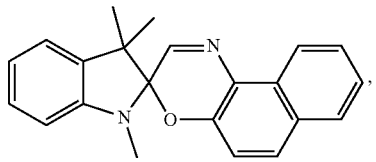
4

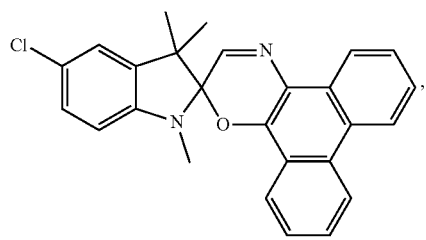
6

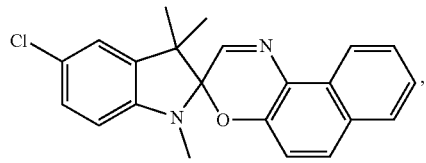
8

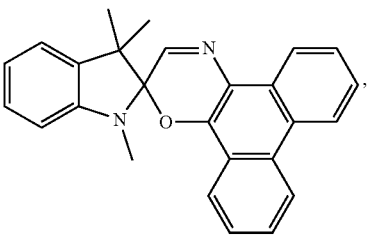
10

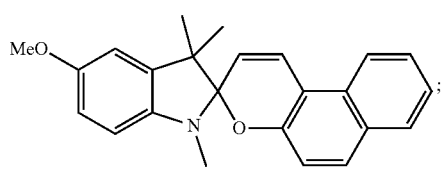
11 wherein the photochromic colorant confers to the composite a reversible strain-induced color change property, further wherein the composite has a flexural modulus in the range of from less than 2 GPa to about 0.1 GPa.

11. The method of claim 10, further comprising grinding the composite into pellets.

12. The method of claim 11, further comprising extruding the pellets in a melt extruder to provide a filament.

13. The method of claim 10, wherein the photochromic colorant has the structure of Formula 1:

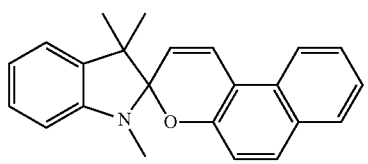

14. The method of claim 10, wherein the photochromic colorant is present in an amount in a range from about 0.1 percent by weight of the composite to about 5.0 percent by weight of the composite.

15. A coated cable comprising a cable coating that permits visual detection of mechanical stresses in a wire, wherein the cable coating comprises a composite comprising:
   an acrylonitrile-butadiene-styrene matrix wherein the ratio of acrylonitrile:butadiene:styrene is from about 15 to about 35 weight %:about 5 to about 30 weight %:about 40 to about 60 weight %, respectively; and
   a photochromic colorant having any one of the following structures:

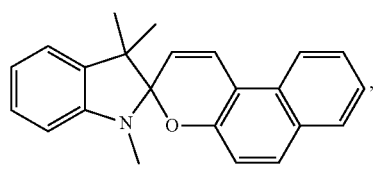

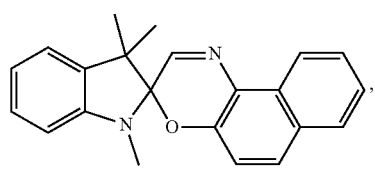

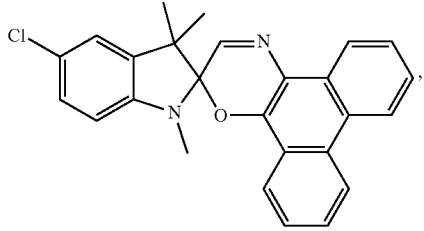

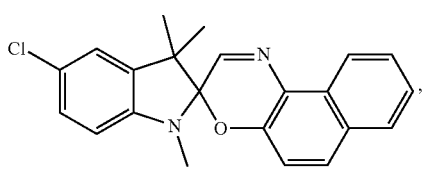

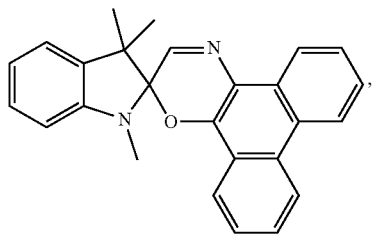

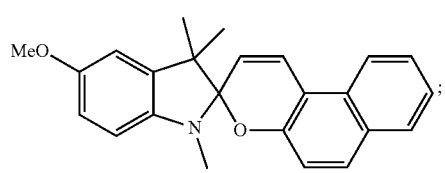

wherein the photochromic colorant confers to the composite a reversible strain-induced color change property further wherein the composite has a flexural modulus in the range of from less than 2 GPa to about 0.1 GPa.

16. The coated cable of claim 15, wherein the photochromic colorant is reversible with respect to light-induced color change.

17. The coated cable of claim 15, wherein the photochromic colorant has the structure of Formula 1:

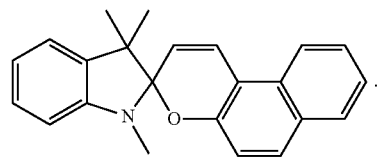

18. The coated cable of claim 15, wherein the photochromic colorant is present in an amount in a range from about 0.1 percent by weight of the composite to about 5.0 percent by weight of the composite.

19. The coated cable of claim 15, wherein reversible strain-induced color change property is reversible by applying heat to the cable coating.

20. The coated cable of claim 15, wherein the coating has a thickness in a range from about 0.1 mm to about 5 mm.

* * * * *